March 28, 1972 ST. J. TOY Plant Pat. 3,085
ALMOND TREE
Filed Feb. 9, 1970
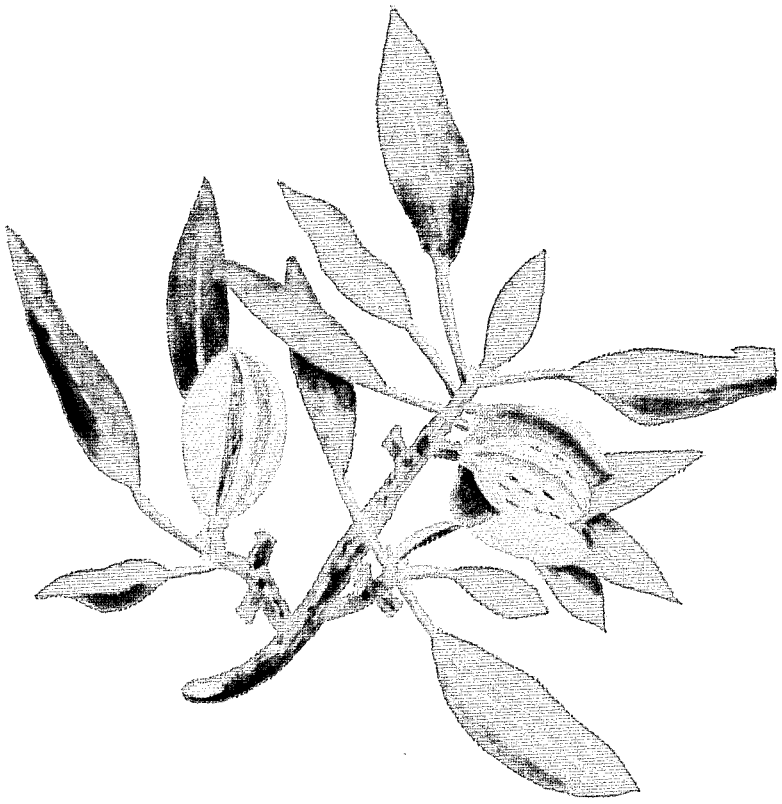
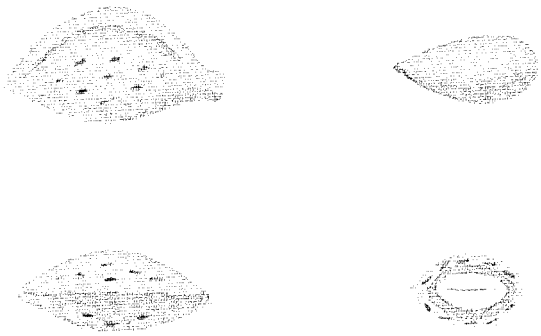
St. Joseph Toy

United States Patent Office

Plant Pat. 3,085
Patented Mar. 28, 1972

3,085
ALMOND TREE

St. Joseph Toy, Rte. 3, Box 73, Chico, Calif. 95926

Filed Feb. 9, 1970, Ser. No. 10,060
Int. Cl. A01h *5/03*
U.S. Cl. Plt.—30 1 Claim

This discovery relates to a new and distinct variety of almond tree, *Prunus amygdalus* Batsch, which I found in 1964 growing in my orchard, five miles south of Chico, Calif. This tree was recognized by me as outstandingly superior in many respects to the present standard varieties Drake and Mission, which mature about the same time, late in the season. Accordingly, I propagated this tree asexually by grafting and budding onto young established almond trees of other varieties and onto peach and Marianna plum rootstocks, and have found it to reproduce true in all respects.

The bloom time of this tree coincides with Nonpareil, presently the predominant commercial variety in California, and is therefore a superior pollinizer for Nonpareil. The nut maturity time is fairly late and therefore does not interfere during harvest with the early maturing Nonpareil. Yet, it matures appreciably earlier than the late maturing Drake and Mission, thus standing a better chance of escaping early winter rains. This tree is particularly superior to Drake because it is resistant to blossom brown rot and the nuts are more easily knocked from the tree; it is superior to Mission because it is less susceptible to Ceratocystis canker and has a larger bearing surface due to the more widely branching tree. The nut is superior to both Drake and Mission because of a substantially higher kernel content.

The distinguishing characteristics of this new variety are as follows:

Tree:

*Shape.*—Medium spreading, like Nonpareil.
*Bark.*—Grayish when mature, texture like Nonpareil.
*Leaves.*—Medium size, petiole length 22 mm.; blade 70 mm. long and 21 mm. wide, slightly recurved, margin slightly undulate; glands globose.
*Growth.*—Vigorous, bears heavily when young.

Flower:

*Bloom time.*—Same as Nonpareil.
*Quantity.*—Very heavy.

*Compatibility.*—Cross fertile with Nonpareil, Ne Plus Ultra, Drake and Mission.

Nut:

*Size.*—Medium, 1.75 grams.
*Hull.*—Thin, 1.0 mm. thick.
*Shell.*—Soft, well sealed, 2.0 mm. thick.
*Shape.*—Like Nonpareil but slightly thicker, has a pronounced neck at point of attachment to pedicel.
*Bearing.*—Heavy, bears consistently every year under normal conditions.
*Maturity time.*—Medium late, midway between Ne Plus Ultra and Mission.

Kernel:

*Size.*—Medium, 1.0 gram.
*Shellout.*—High, 55 to 60%.
*Shape.*—Like Nonpareil but slightly more plump, 22 mm. long, 12 mm. wide, 9 mm. thick.
*Color.*—Medium, like Drake.
*Pellicle.*—Thin, surface medium smooth.
*Flavor.*—Sweet, sometimes with a slight almond flavor.

The top of the drawing shows a fruiting twig with leaves, fruit spurs and two nuts. The nuts shown attached to the twig are at the stage just prior to harvest when the exocarp has dehisced. The bottom of the drawing shows various aspects of the nut, illustrating both shell and kernel and their relative proportions and shape. The dissected view is a transverse section through the nut, showing a cross section of the kernel and the relative thickness of the shell.

This variety may vary somewhat from the description and drawing, depending on season, location and soils. The named varieties mentioned for comparison are all standard unpatented varieties that have been grown for many decades in California.

Having thus described my discovery, I claim:

1. A new and improved variety of almond tree characterized by more favorable bloom time, heavier bearing, higher kernel content, greater disease resistance, and more favorable harvest characteristics than present late maturing varieties.

No references cited.

ROBERT E. BAGWILL, Primary Examiner